US011553882B2

(12) United States Patent
Wu et al.

(10) Patent No.: US 11,553,882 B2
(45) Date of Patent: *Jan. 17, 2023

(54) TRANSPORT APPARATUS IN MEDICAL SYSTEM

(71) Applicant: SHANGHAI UNITED IMAGING HEALTHCARE CO., LTD., Shanghai (CN)

(72) Inventors: Jing Wu, Shanghai (CN); Yining Wang, Shanghai (CN); Bo Li, Shanghai (CN); Xiangming Hou, Shanghai (CN); Yunlei Yao, Shanghai (CN); Jian Liu, Shanghai (CN); Xiwei Dai, Shanghai (CN); Hongtao Ren, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 357 days.

This patent is subject to a terminal disclaimer.

(21) Appl. No.: 16/662,298

(22) Filed: Oct. 24, 2019

(65) Prior Publication Data
US 2020/0085379 A1  Mar. 19, 2020

Related U.S. Application Data

(63) Continuation of application No. 15/317,539, filed as application No. PCT/CN2015/094461 on Nov. 12, 2015, now Pat. No. 10,548,532.

(30) Foreign Application Priority Data

Nov. 12, 2014  (CN) .................. 201410635873.X
Feb. 11, 2015  (CN) .................. 201520100198.0
(Continued)

(51) Int. Cl.
A61B 5/00       (2006.01)
A61B 6/03       (2006.01)
(Continued)

(52) U.S. Cl.
CPC ............... *A61B 5/70* (2013.01); *A61B 5/055* (2013.01); *A61B 5/704* (2013.01); *A61B 6/03* (2013.01);
(Continued)

(58) Field of Classification Search
CPC ........... A61B 5/055; A61B 5/70; A61B 5/704; A61B 6/03; A61B 6/037; A61B 6/0407; A61B 6/0487; A61B 6/4417; A61G 13/06
See application file for complete search history.

(56) References Cited

U.S. PATENT DOCUMENTS 3,532,882 A   10/1970  Craig et al.
3,588,500 A *  6/1971  Koerner ............... A61B 6/0487
                                                       5/601
(Continued)

FOREIGN PATENT DOCUMENTS

CN   102359643 A   2/2012
CN   103006253 A   4/2013
(Continued)

OTHER PUBLICATIONS

International Search Report in PCT/CN2015/094461 dated Feb. 16, 2016, 5 Pages.
(Continued)

*Primary Examiner* — David R Hare
(74) *Attorney, Agent, or Firm* — Metis IP LLC

(57) ABSTRACT

A transport apparatus may include a patient bed unit for supporting the patient; a transferring unit for moving the patient bed unit along a first direction of the MRI device; and
(Continued)

an elevating module for moving the patient bed unit along a second direction of the MRI device.

20 Claims, 16 Drawing Sheets

(30) Foreign Application Priority Data

Feb. 12, 2015 (CN) .......................... 201520102703.5
Jul. 24, 2015 (CN) .......................... 201510443621.1

(51) Int. Cl.
*A61B 6/04* (2006.01)
*A61B 6/00* (2006.01)
*A61B 5/055* (2006.01)
*A61G 13/06* (2006.01)

(52) U.S. Cl.
CPC ............ *A61B 6/037* (2013.01); *A61B 6/0407* (2013.01); *A61B 6/0487* (2020.08); *A61B 6/4417* (2013.01); *A61G 13/06* (2013.01)

(56) References Cited

U.S. PATENT DOCUMENTS

| | | | |
|---|---|---|---|
| 4,567,894 A | | 2/1986 | Bergman |
| 4,773,637 A | * | 9/1988 | Jarin .................... A61B 6/0487 5/600 |
| 4,984,774 A | * | 1/1991 | Zupancic ............. A61B 6/0487 5/601 |
| 5,210,893 A | * | 5/1993 | Uosaki ................. A61B 5/055 5/601 |
| 5,272,776 A | | 12/1993 | Kitamura |
| 5,273,043 A | | 12/1993 | Ruike |
| 5,490,297 A | | 2/1996 | Bradcovich et al. |
| 5,602,516 A | | 2/1997 | Parfitt |
| 5,808,468 A | | 9/1998 | Bis et al. |
| 5,825,843 A | | 10/1998 | Kobayashi |
| 6,424,854 B2 | | 7/2002 | Hayashi et al. |
| 6,637,056 B1 | | 10/2003 | Tybinkowski et al. |
| 6,776,527 B1 | | 8/2004 | Tybinkowski et al. |
| 6,955,464 B1 | | 10/2005 | Tybinkowski et al. |
| 7,437,785 B2 | | 10/2008 | Farooqui |
| 7,602,189 B2 | | 10/2009 | Decke et al. |
| 7,874,030 B2 | | 1/2011 | Cho et al. |
| 8,467,847 B2 | | 6/2013 | Caruba et al. |
| 8,931,125 B2 | | 1/2015 | Fang et al. |
| 9,433,349 B2 | | 9/2016 | Emaci et al. |
| 10,548,532 B2 | * | 2/2020 | Wu .......................... A61B 5/70 |
| 2005/0204472 A1 | | 9/2005 | Gagneur et al. |
| 2007/0035301 A1 | | 2/2007 | Toshiba et al. |
| 2007/0143921 A1 | | 6/2007 | Toshiba et al. |
| 2007/0191706 A1 | | 8/2007 | Calderon et al. |
| 2008/0106262 A1 | | 5/2008 | Toshiba et al. |
| 2008/0235874 A1 | * | 10/2008 | Grosshauser .......... A61B 5/055 5/601 |
| 2009/0070935 A1 | * | 3/2009 | Brunker .................. H02P 31/00 5/601 |
| 2010/0148775 A1 | | 6/2010 | Greim |
| 2011/0047700 A1 | * | 3/2011 | Klemm ................ A61B 6/0487 5/600 |
| 2013/0176029 A1 | | 7/2013 | Oosawa |
| 2013/0181716 A1 | | 7/2013 | Greim |
| 2014/0088403 A1 | | 3/2014 | Gross |
| 2014/0088404 A1 | * | 3/2014 | Gross ..................... A61B 5/062 600/411 |
| 2015/0196227 A1 | | 7/2015 | Chen et al. |
| 2015/0208946 A1 | * | 7/2015 | Popescu ............... A61B 6/0428 600/415 |

FOREIGN PATENT DOCUMENTS

| | | |
|---|---|---|
| CN | 203369915 U | 1/2014 |
| CN | 203458383 U | 3/2014 |
| CN | 104134574 A | 11/2014 |
| GB | 2185627 A | 7/1987 |
| JP | H0341932 A | 2/1991 |
| JP | 2010017457 A | 1/2010 |

OTHER PUBLICATIONS

First Office Action for Chinese Application No. 201410635873.X dated Mar. 19, 2019, 15 pages.
First Office Action for Chinese Application No. 201510443621.1 dated Sep. 4, 2019, 16 pages.

* cited by examiner

TRANSPORT APPARATUS IN MEDICAL SYSTEM

CROSS-REFERENCE TO RELATED APPLICATIONS

This application is a continuation of U.S. application Ser. No. 15/317,539, which is a U.S. national stage under 35 U.S.C. § 371 of International Application No. PCT/CN2015/094461, filed on Nov. 12, 2015, which claims priority of Chinese Patent Application No. 201410635873.X filed on Nov. 12, 2014, Chinese Patent Application No. 201520100198.0 filed on Feb. 11, 2015, Chinese Patent Application No. 201520102703.5 filed on Feb. 12, 2015, Chinese Patent Application No. 201510443621.1 filed on Jul. 24, 2015, the entire contents of each of which are hereby incorporated by reference.

TECHNICAL FIELD

The present disclosure generally relates to a transport apparatus, and more specifically to a transport apparatus used in connection with a medical system.

BACKGROUND

The present disclosure relates generally to a transport apparatus, and particularly, a transport apparatus and method for transferring and/or positioning a patient in the medical system. The medical system may be, for example, a medical imaging system (for example, a magnetic resonance imaging (MRI) system), a treatment system, an examination system, or the like, or a combination thereof. For instance, an MRI device may be used to obtain tomographic images of a biological tissue in, for example, a patient, using a magnetic field generated by magnetic force; to this end, a magnetic field may be applied to the body of the patient who lies on a table device that has been transferred into the MRI device.

The table device used for relocating a patient may be referred to as a gurney or stretcher. A patient may be transported upon a gurney into and/or out of a medical imaging system such as an MRI device. The table device used in a medical imaging system, for example, an MRI environment, may have several features. For example, the table device may need to be used in a strong electromagnetic environment. As another example, an examination bed may be used for transporting a patient into the medical imaging system and in some cases bringing him into his room when the examination is over. It is then necessary to lift the patient and move the patient to the exact location to be imaged in the medical device.

SUMMARY

The present disclosure generally relates to a transport apparatus, and more specifically to a transport apparatus used in connection with a medical system. Merely by way of example, the transport apparatus may be used in connection with an MM device. The transport apparatus may be used to move a patient horizontally and vertically in an efficient and accurate way.

The present disclosure also relates to a method of positioning a patient within a gap in an Mill scanner. The method may include lifting a patient bed unit and inserting the patient bed unit into the bore of the Mill device.

A further aspect of the present disclosure provides a transport apparatus for moving a patient. The transport apparatus may include: a patient bed unit for supporting the patient; a transferring unit for moving the patient bed unit along a first direction of the Mill device; and an elevating module for moving the patient bed unit along a second direction of the Mill device.

According to one aspect of the present disclosure, the transferring unit of the transport apparatus may include one or more sliding rollers.

According to one further aspect of the present disclosure, the transferring unit of the transport apparatus may include one or more buffer rollers. The radius of one of the one or more buffer rollers may be smaller than or equal to the radius of one of the one or more sliding rollers.

According to one further aspect of the present disclosure, the number of sliding rollers may be even.

According to one further aspect of the present disclosure, the radius of the buffer rollers may be at least 10 mm smaller than that of the sliding rollers.

According to one further aspect of the present disclosure, the radius of the buffer rollers may be at least 8 mm smaller than that of the sliding rollers.

According to one further aspect of the present disclosure, the radius of the buffer rollers may be at least 5 mm smaller than that of the sliding rollers.

According to one further aspect of the present disclosure, the radius of the buffer rollers may be at least 2 mm smaller than that of the sliding rollers.

According to one further aspect of the present disclosure, the bed transferring unit may include a drag chain structure.

According to one further aspect of the present disclosure, the drag chain structure may include a bent part that may move in a third direction when the patient bed unit moves in a fourth direction, in which the third direction may be opposite to the fourth direction.

According to one further aspect of the present disclosure, the patient bed unit may include a line trapper. The line trapper may be of, for example, an elliptic shape.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
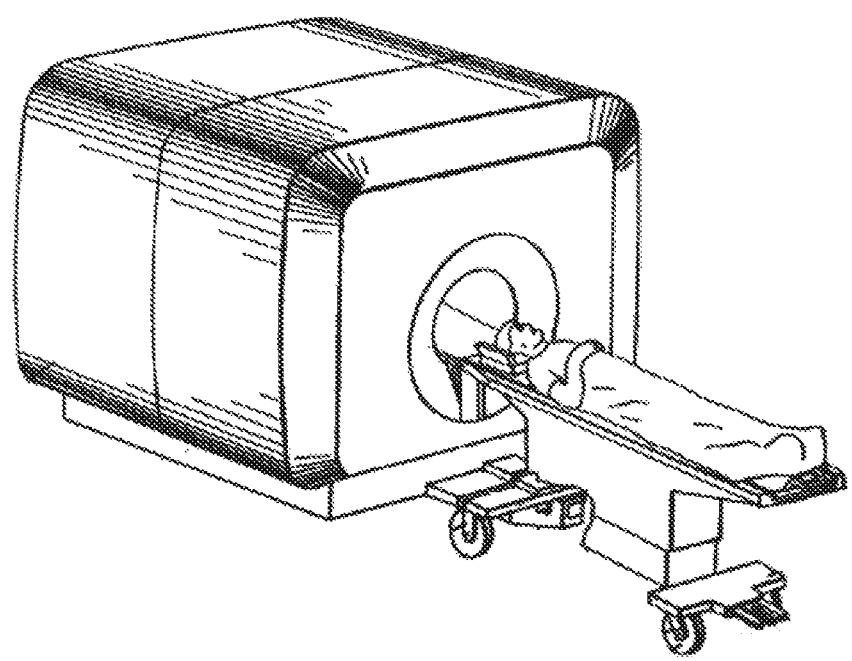
FIG. 1 is a schematic diagram of an exemplary transport apparatus in accordance with some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to," or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale. Also, it is understood by one of ordinary skill in the art that the MRI device illustrated below may further include other commonly used elements.

The present disclosure relates to a medical system for examination, imaging, and/or treatment of a patient. For brevity, an examination system or imaging system as used herein may also refer to a treatment system. The medical system may include a device for examination, imaging, and/or treatment, a patient support and/or transport apparatus, and possibly a docking structure or mechanism for connecting both together.

The system may be a medical imaging system. Merely by way of example, the system may be an MRI device in which images may illustrate or provide information relating to a biological tissue or an organ of a patient using a magnetic resonance imaging method. The examination device of such a system may include an electrical coil system for generating a varying magnetic field and radio-frequency signals in an examination volume, in which the patient may be placed. The electrical coil system may also receive radio-frequency signals generated by the body of the patient in response to the radio-frequency signals generated by the electrical coil system.

A patient support device may be used to transport or support a patient. The patient support device may include a trolley with a patient bed unit, on which the patient may lie. By making use of a docking structure, the trolley may be connected to the examination device, after which the bed may be displaced from the trolley and may be moved into the examination volume of the examination device, so that an examination may be performed on the patient. After examination, the bed may be displaced from the examination device and connected to the trolley, so that the patient support device may be moved away.

Before the patient support device may be connected to the examination device, the patient support device may need to be placed at a specific location and in a specific position with respect to the examination device. The patient support device may be moved to the specific location and/or the specific position manually by, for example, an operator, by an automated operation, or the like, or a combination thereof. For instance, the patient support device may be moved to a location within a range of the specific location manually by an operator, and the adjustment of the location and/or position of the patient support device may be performed by an automated operation.

In some embodiments of the present disclosure, a docking structure for connecting a patient support device to an examination device is provided. The docking structure may include a guiding member. The docking member may include one or more guiding surfaces. The guiding surfaces may be positioned symmetrically with respect to the patient bed unit, thus facilitating the attachment of the docking member to the examination device.

A specific medical imaging environment may also need to be considered for a patient transport apparatus. For example, when a patient is examined in an imaging system having a bore or a gantry, such as a magnetic resonance tomography system or a Positron Emission Tomography (PET) system, the patient may need to be supported on a patient bed unit and moved into the bore. The spatial extension of the bore may be in the form of a hollow cylinder with an external diameter of approximately 2 meters. The patient bed unit may need to be at a distance of between 70 and 90 cm from the ground to be moved into the bore. For a patient to be able to climb relatively easily onto the patient bed unit, however, the patient bed unit may be approximately 55 cm or less from the ground. It is understood that these dimensions are provided for illustration purposes. Different dimensions may be appropriate for patients of various height and/or for medical imaging systems of different sizes. A vertically adjustable patient transport apparatus may be needed.

A patient transport apparatus that may be operated in a mobile manner may be desirable. For instance, for an imaging system operated according to the magnetic resonance principle including, for example, a magnetic resonance tomography system or an MR/PET system, a strong magnetic field may be present in the examination region; a patient may not be moved directly into the examination space using a patient support device used for general hospital transportation (for example, a patient couch, a trolley, a hospital bed, etc.). With a patient transport apparatus that may be used in a mobile way, the patient may be safely transferred, for example, from a hospital trolley to the patient transport apparatus that may be connected to the medical device in a magnetic field-free space (preparation space).

A patient transport apparatus may include a servo dynamical system to facilitate the vertical adjustment and movement of the patient. A servo dynamical system may be realized as electric or hydraulic lifting systems. An electric lifting system may include an electric motor. An electric lifting system may include an energy storage unit (battery or accumulator) when deployed in a mobile manner. A hydraulic lifting system may include a lifting piston. The lifting piston may include a pressurized hydraulic fluid (for example, a hydraulic oil). A hydraulic lifting system may provide an efficient means of manual adjustment by way of, for example, foot pedals in conjunction with a piston pump. Specific description of the servo dynamical systems will also be addressed at the appropriate section of current disclosure.

A mobile patent transport apparatus may also promote the use efficiency of a medical imaging system. For instance, while one patient is undergoing examination, another may be prepared for examination in a preparation room. A mobile patent transport apparatus may also be advantageous in situations where a patient may need to be removed from the medical imaging system (as in an emergency) and to transport the patient with a minimum delay to an area where assistance in the form of, for example, support equipment and/or care, is available.

FIG. 1 is a schematic diagram of an exemplary magnetic resonance imaging (MRI) system. FIG. 1 illustrates a patent transport apparatus generally for supporting and positioning a patient relative to a medical system such as a nuclear magnetic resonance (NMR) machine. The NMR machine includes an outer enclosure housing a magnet that generates images of a specific portion of the body of a patient. The patient may be received within an opening formed in the NMR machine during a scanning procedure. The patent transport apparatus may include a patient bed unit, a servo dynamical system, and a latching mechanism for cooperation with patient transport described below. Although FIG. 1 illustrates a transport apparatus for supporting and positioning a patient relative to the NMR machine, it is readily apparent that the transport apparatus is a mobile vehicle that may be employed for supporting and positioning other loads. Thus, the transport apparatus may be used with other medical imaging systems in various types of applications.

Figure 2:
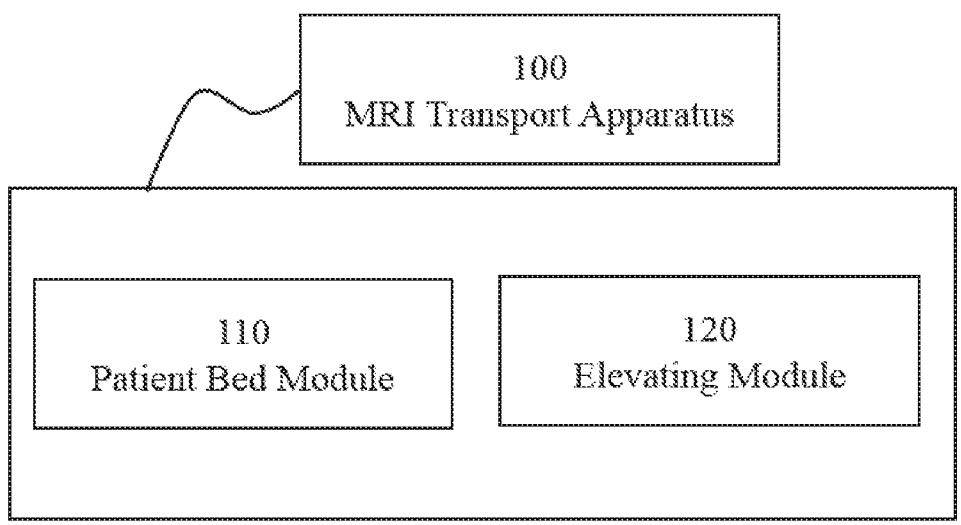
FIG. 2 is a block diagram of an exemplary transport apparatus in accordance with some embodiments of the present disclosure.
Figure 3:
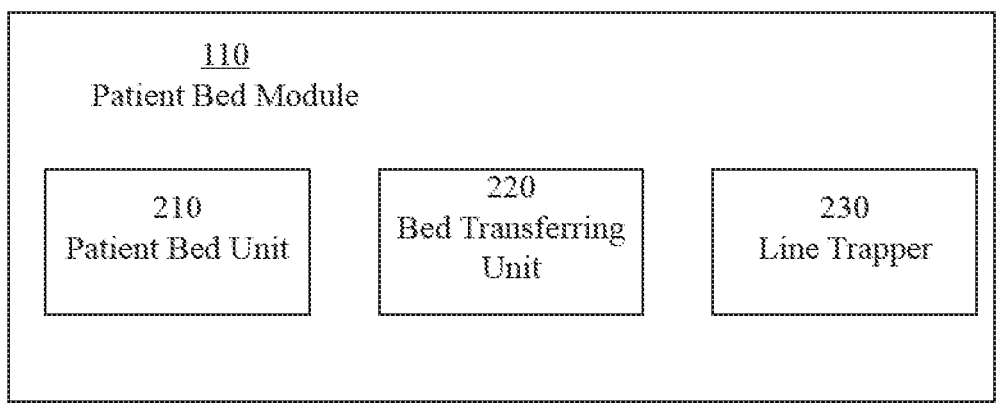
FIG. 3 is a block diagram of an exemplary patient bed module in accordance with some embodiments of the present disclosure.

FIGS. 2 and 3 give exemplary block diagrams of a transport apparatus in accordance with some embodiments of the present disclosure. The transport apparatus may be used with an MRI device. The transport apparatus may include a patient bed module 110, and an elevating module 120. The patient bed module 110 may be used to move a patient into and out of an MM device. The patient bed module 110 may be configured to protect the patient in an electro-magnetic environment, and/or facilitate the movement of the patient into and out of the Mill device. The patient bed module 110 may include a patient bed unit 210, a bed transferring unit 220, and a line trapper 230. A patient may lie on the patient bed unit 210 so as to allow transportation of the patient from, for example, one imaging system to another imaging system, or to enter or exit the bore of the Mill device. The bed transferring unit 220 may be used to transfer the patient into or out of the bore of the Mill device. The patient bed unit 210 may be equipped with one or more line trappers 230. A line trapper 230 may be used to prevent the damage of the high power current induced by the RF signal of the Mill device to the patient.

Figure 4:
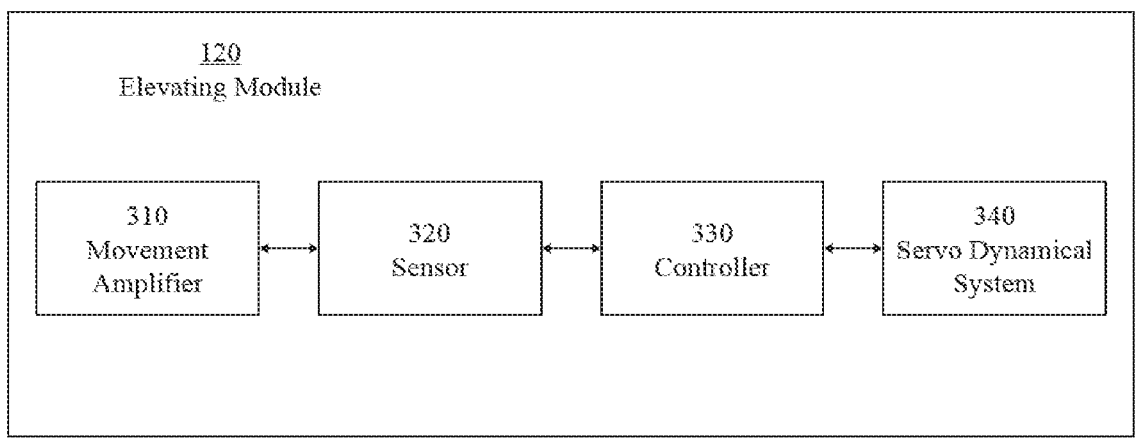
FIG. 4 is a block diagram of an exemplary elevating module in accordance with some embodiments of the present disclosure.

FIG. 4 is an exemplary block diagram of the elevating module in accordance with some embodiments of the present disclosure. The elevating module 120 may include a movement amplifier 310, a sensor 320 to detect the motion or movement of the patient bed unit 210, a controller 330. The controller 330 may receive feedback from the movement amplifier 310 and/or the sensor 320. The controller 330 may send a command to the movement amplifier 310, and/or the sensor 320, and/or the servo dynamical system 340 to control the movement of the patient bed unit 210. The servo dynamical system 340 may be of a hydraulic type, or an electric type, or the like, or any combination thereof. Merely by way of example, a patient may be supported on a computer controlled, movable patient bed unit which is activated by a servo dynamical system of electric type. The patient bed unit 210 may be moved or translated fore and aft through the bore of the Mill device. Thus, a patient may be selectively positioned within the bore of the main magnet and the motion of the patient bed units under the control of, for example, a computer. Additionally, the transport apparatus may be designed to allow movement of patient bed unilaterally and/or vertically as directed by the operator.

Figure 5:
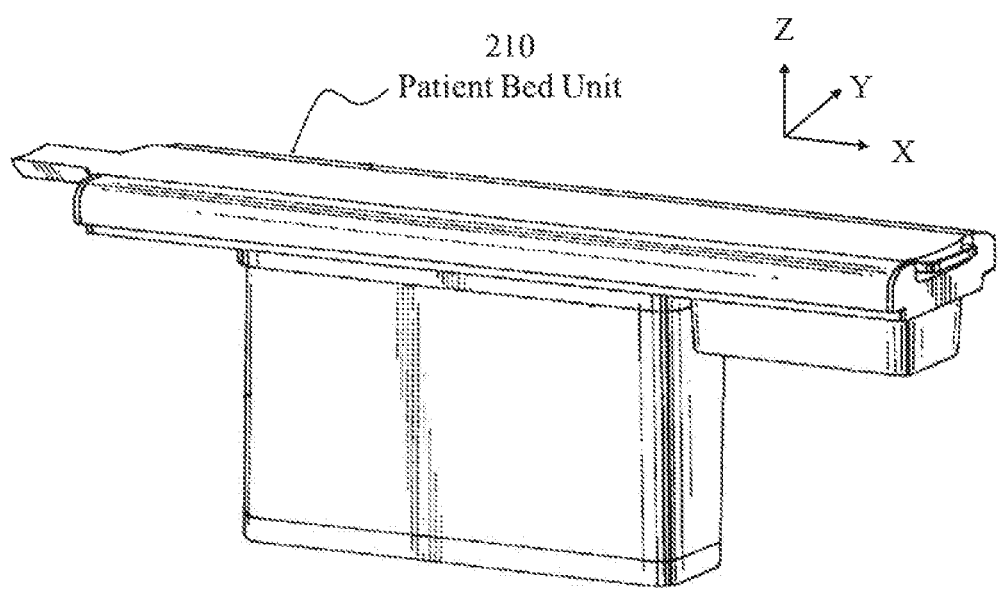
FIG. 5 is a schematic diagram of an exemplary patient bed unit in accordance with some embodiments of the present disclosure.

FIG. 5 is a perspective view of an exemplary patient bed unit 210. As illustrated, the patient bed unit is in the fully raised position. The patient bed unit may be supported on an elevating module 120 (invisible in FIG. 5) as disclosed in the present disclosure. The elevating module 120 may be used to lift a patient on the patient bed unit vertically (parallel with the x-axis) to a desired position with respect to the rotation axis (z-axis) of the bore before a scanning procedure begins. Among other advantages, the elevating module 120 may move the patient bed unit both vertically (parallel with the x-axis) and horizontally (parallel with the z-axis). The elevating module 120 may also nest in its lowered position in order to reduce or minimize the patient bed unit's overall height when lowered.

In some embodiments, the patient bed unit 210 may be movable horizontally by the bed transferring unit 220. The bed transferring unit 220 may include, but not limited to, guiding members, a chassis, and rollers (see FIGS. 6 and 7 for further description regarding this aspect). The patient bed unit 210 may be movable with respect to the chassis via the coordination of the guiding members and/or the rollers. The guiding members may guide the movement of the patient bed unit before it reaches its final position.

Figure 6:
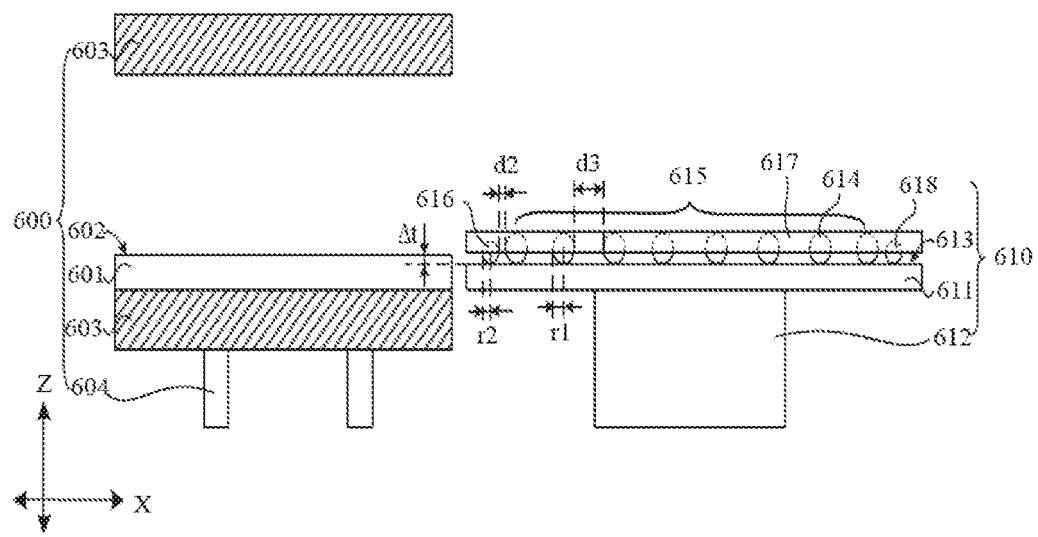
FIG. 6 is another schematic diagram of an exemplary patient bed unit in accordance with some embodiments of the present disclosure.
Figure 7:
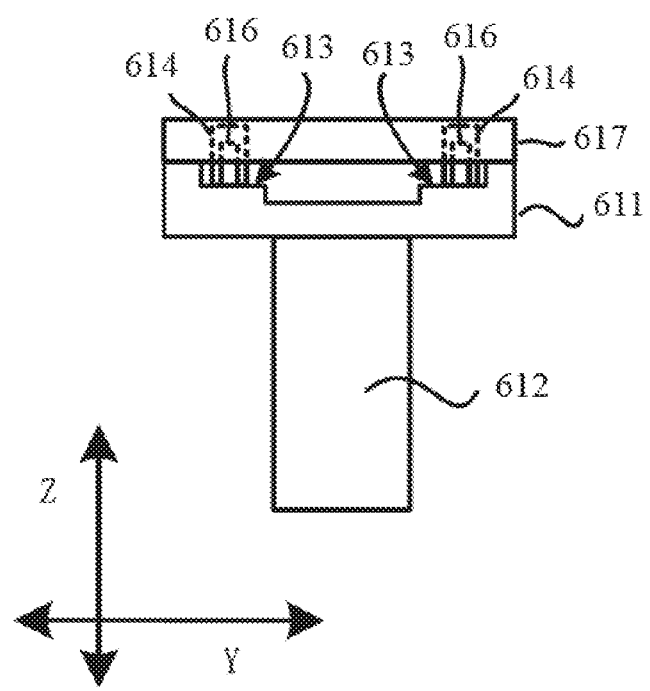
FIG. 7 is another view of the schematic diagram of an exemplary patient bed unit as in FIG. 6 in accordance with some embodiments of the present disclosure.

FIG. 6 is the cross-sectional view of MRI device and a patient bed module in accordance with some embodiments of the present disclosure. FIG. 7 is a left view of a patient bed module in accordance with some embodiments of the present disclosure.

As shown in FIG. 6, the patient bed unit 610 may include a bed board 617 for accommodating a patient, a bedstead 611 for supporting the bed board 617, two sliding wheel sets 615 for allowing the bed board 617 to move horizontally along the longitudinal direction (i.e. along x-axis) of the bed board 617 relative to the bedstead 611. The two sets of sliding wheels 615 may be located on the sides of the width (i.e. along y-axis) of the bed board 617, respectively. The sliding wheel sets 615 may include one or more sliding rollers 614 along the longitudinal direction of the bed board 617. In some embodiments, the sliding wheel sets 615 may include one or more buffer rollers 616 along the longitudinal direction of the bed board 617. In some embodiments, at least one buffer roller may be located fore and/or aft the set of the sliding rollers 614. In some embodiments, the patient bed unit 610 may also include the chassis 612 connected to and/or supporting the bedstead 611.

Merely for illustration purposes, in FIG. 6, the x-axis points to the longitudinal direction of the bed board 617, whereas the y-axis points to the width-wise direction of the bed board 617, and the z-axis points to the upward direction perpendicular to the plane spanned by the x-axis and the y-axis.

In some embodiments, the number of the sliding rollers 614 may be more than two. For example, the number of the sliding rollers 614 may be 4, 5, 6, 7, 8, or more than 8. The number of the sliding rollers 614 may be an even number. In some embodiments, the sliding rollers may be mounted on the bed board 617. In some embodiments, the sliding rollers may be mounted on the bedstead 611. The distribution of the sliding rollers 614 may be symmetrical or asymmetrical along the longitudinal direction of the bed board 617. For instance, the sliding rollers 614 may be distributed symmetrically along the longitudinal direction of the bed board 617. In some embodiments, the sliding rollers 614 may be distributed symmetrically along the width direction (y-axis direction) of the bed board 617.

The buffer rollers 616 and 616' may be designed so as to facilitate the transport of a patient. In some embodiments, the buffer roller 616 may be mounted on either side of the bed board 617 along the longitudinal direction of the bed board, facing the bedstead 611. The radius of a sliding roller 614 may be set as r1. The radius of a buffer roller 616 may be set as r2. In some embodiments, the radii of all the sliding rollers 614 may be equal. In some other embodiments, the radii of at least two sliding rollers 614 may be different. For example, the radii of the sliding rollers may be distributed in a symmetrical way along the longitudinal direction of the bed board 617. The radius of a buffer wheel 616 r2 may be less than or equal to the radius of a sliding roller 614 r1. In some embodiments, a sliding wheel set may have the buffer roller located symmetrically with respect to the bedstead along the longitudinal direction of the bed board 617. As illustrated in FIG. 6, the buffer roller 616 and the buffer roller 618 are located symmetrically with respect to the bed stead 612.

The distance between the buffer roller 616 and the sliding roller 614 next to the buffer roller 616 may be designated as a first distance d1 The distance between a pair of neighboring sliding rollers 614 (next to each other) along the longitudinal direction (x-axis direction) may be designated as a second distance d2. In some embodiments, the second distance d2 may be greater than or equal to the first distance d1, so that it may absorb the force caused by the impact. In some embodiments, the first distance d1 may be within the range from 1 mm to 10 mm, or from 2 mm to 8 mm, s or from 5 mm to 8 mm.

In some embodiments, there may be two buffer rollers 616 and 618 on the bed board 617 along the longitudinal direction. The two buffer rollers 616 may be spaced apart. The sliding roller set 615 may be located between the two buffer rollers 616. The two buffer rollers 616 and 616' may be spaced apart symmetrically on both sides of the sliding roller set 615.

One or more guide rails may be utilized to facilitate the movement of a sliding roller 614 and/or a buffer roller 616. In some embodiments, on the side of the bed board 617 facing the bedstead 611, there may lie a first guide rail 613 that may guide or stabilize the movement of the sliding roller set 615 and the buffer rollers 616. The sliding rollers 614 and the buffer rollers 616 may be restricted by the first guide rail 613 to move substantially along the longitudinal direction of the bed board 617. In some embodiments, as illustrated in FIG. 7, the bedstead 611 may have two first guide rails 613 that may provide guidance or support for the two sliding roller sets 615 and the buffer rollers 616.

Returning to FIG. 6, the patient bed module 610 may be used in combination with a medical imaging device. As illustrated in FIG. 6, the Mill scanning device 600 may lie on the left side of the bedstead 611. The scanning device 600 may include a first bed board support 601, a magnet 603, and a magnet support 604. The magnet support 604 may provide support for the magnet 603. The bed board support 601 may be located in an aperture or bore of the magnet 603. When at least a part of the bed board 617 slides off the bedstead 611, part of the bed board 617 may slide horizontally along the longitudinal direction onto the bed board support 601, so that the patient on the bed board 617 may be sent into the aperture or bore of the magnet 603. In some embodiments, a second guide rail 602 may be set on the bed board support 601. The sliding rollers 614 and the buffer rollers 616 may slide along the second guide rail 602. The guide rail 613 or 602 may be made of, for example, plastic, metal, or the like, or a combination thereof. For instance, the guide rail 613 or 602 may be made of, stainless steel, aluminum, or the like, or an alloy thereof, or any combination thereof. As another example, the guide rail 613 or 602 may be made of, a polymer.

As shown in FIG. 6, when the patient lies on the bed board 617, before the bed board 617 enters the aperture or bore of the magnet 603, the upper surface of the first guide rail 613 may be lower than the upper surface of the second guide rail 602 because of the weight of the patient. The altitude difference between the upper surface of the first guide rail 613 and the upper surface of the second guide rail 602 may be denoted by $\Delta t$. To accommodate this altitude difference, the radius r2 of the buffer rollers 616 may be different from the radii r1 of the sliding rollers 614. In some embodiments, the centers of the buffer rollers 616 and the centers of the sliding rollers 614 may be at the same horizontal level; the difference in the radius r1 and the radius r2 may be equal to or greater than the altitude difference Δt so that the buffer rollers 616 may absorb the impact caused to the patient. The comfort of the patient may be improved and the lifespan of the sliding wheels 614 may be prolonged. In some embodiments, the radius difference and the altitude difference Δt may be equal to or less than 3 mm, or 2 mm, or 1 mm.

Figure 8:
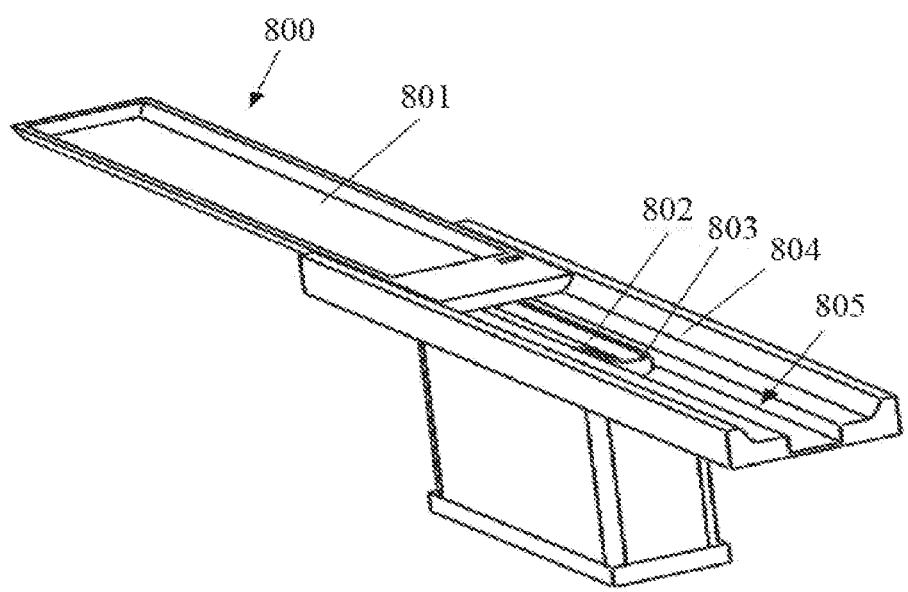
FIG. 8 is another schematic diagram of an exemplary patient bed unit in accordance with some embodiments of the present disclosure.

Another illustrating example of a patient bed module 110 is given in FIG. 8, in which the bed transferring unit 220 may include a drag chain 802. The drag chain 802 may lie upon the bed stead 804. The whole drag chain 802 may be set in a second groove 805 of the bedstead 804 A first end of the drag chain 802 may be fixed upon the bed board 801, and a second end of the drag chain 802 may be fixed upon the second groove 805 (which is not shown in this figure). The attachment of the drag chain 802 onto the bed board 801 and the second groove 805 may be such that, when the bed board 801 moves along the longitudinal direction of the bedstead 804 towards the bore of the MRI device (and away from the bedstead 804), the bed board 801 may move the first end of the drag chain 802 with respect to the second end of the drag chain 802, rendering the bent part 803 of the drag chain 802 away from the bed board 801 gradually. The bent part 803 may then remain away from the bore of the MRI device, even when the bed board 801 has been near to or entered the aperture of the MRI device.

Figure 9:
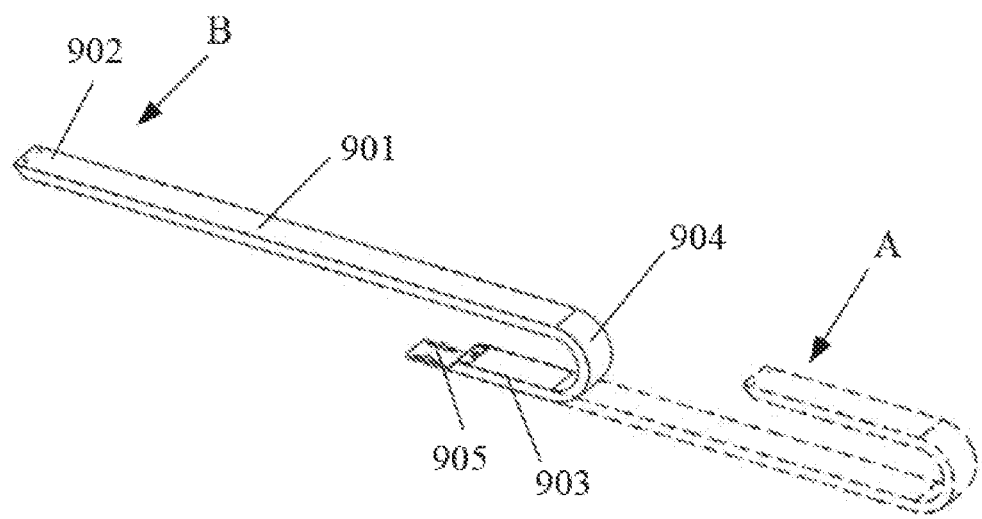
FIG. 9 is a schematic diagram of an exemplary transport chain mechanism in accordance with some embodiments of the present disclosure.

To illustrate the mechanism of drag chain structure in transferring unit, refer to FIG. 9. FIG. 9 is the schematic diagram of the status of the drag chain when the bed board 801 with the drag chain 802 moves in the longitudinal direction of the bed board 801. The first end 902 of drag chain 802 may be fixed upon the bed board 801 via a fastener. The fastener may be a fixture including, for example, a screw, a catch, a buckle, etc. The bent part 904 of the drag chain 802 may become close to the first end 902 of the drag chain 802 when the bed board 801 and the bedstead 804 overlap, one on top of another. As the bed board 801 moves horizontally towards the bore of the MRI device, the position of the first end 902 of the drag chain 802 may be shifted from A to B. Until the whole bed board 801 moves to the external edge of the bedstead 804 (i.e. the bed board 801 entirely enters the bore of the MR system, which is not shown in the figure), the bend part 904 of the drag chain 802 may be in a position away from the bed board 801 (namely, away from the bore of the MRI device). Interference by the bent part 904 of the drag chain 802 with the electro-magnetic field caused by the magnet of the MRI device may be reduced or avoided. Such interference may cause artifacts in a produced medical image.

The patient transport apparatus may need to incorporate one or more cables, such as a coaxial cable, to send a command signal to the MRI device. The patient transport apparatus may need to take into account the potential damage to the tissue of a patient caused by high power current in the coaxial cable that may be induced by the RF signal in the MRI device. Some embodiments of the present disclosure encompass the concept of adjusting the wave impedance of a function conductor that may lie in the patient bed unit, in such a way that the function conductor may have a high wave impedance for frequency ranges corresponding to those for expected interference fields, and correspondingly may damp currents at this frequency. This may be achieved using a sheath wave trap, also referred to as a line trapper. A detailed description of the sheath wave trap or a line trapper will be described elsewhere in the current disclosure. As used herein, the wave impedance is a measure of the wavelength-dependent value of the electrical resistance of a high frequency (HF) cable. In a coaxial cable, the wave impedance may be independent of the cable length, but may depend on the capacitance and inductance per unit length of the HF cable. These values may be a function of the diameter of the internal conductor and the shielding, and/or of the dielectric constants of the dielectric. The capacitance and inductance per unit length of a high frequency (HF) cable may be represented in an equivalent circuit diagram by a series connection of numerous individual inductors and a parallel connection of the same number of capacitors. Disregarding the ohmic resistance, the wave impedance (Z) may result approximately from the square root of the ratio of the inductance to the capacitance.

In some embodiments, the impedance effect of the line trapper may be provided by a capacitor. Alternatively or additionally, the impedance effect may be provided by an inductor and/or a short circuit.

Figure 10:
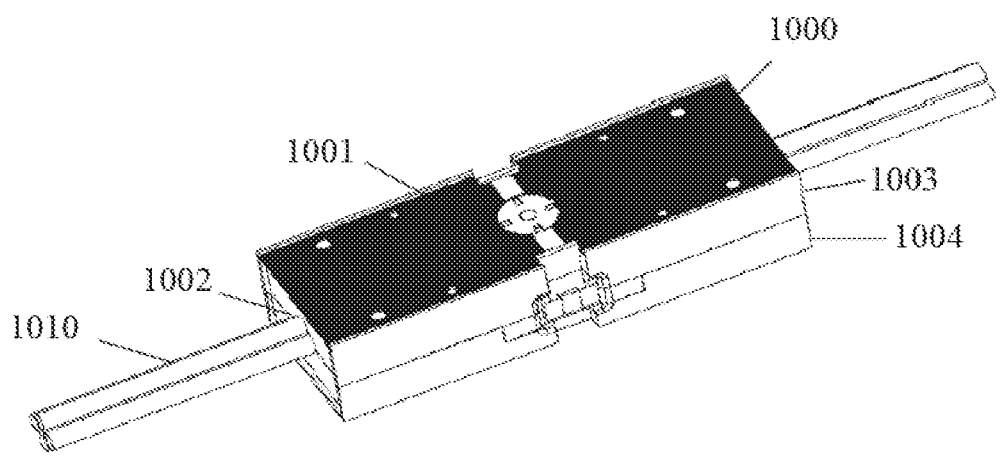
FIG. 10 is a schematic diagram of an exemplary line trapper in accordance with some embodiments of the present disclosure.

As shown in FIG. 10, the sheath wave trap 1000 may include a shell 1001 and a cavity 1002 inside the shell 1001. The sheath wave trap 1000 may be installed in the patient bed unit. Alternatively, the sheath wave trap may be installed in the patient bed module. The cavity 1002 may be configured to accommodate an RF cable 1010. The shell 1001 may act as a mechanical carrier to the electrical elements that are set thereon or therein. In some embodiments, the shell 1001 may be at least partially made of plastic. The plastic may include a feature suitable for use in a magnetic environment. In some embodiments, a metal oxide layer may be injected onto the surface or underneath the surface of the shell 1001. If the metal oxide layer located beneath the outer surface is made of plastic, the shell 1001 may provide electrical insulation and protection in addition to the mechanical stability.

The shell 1001 may include two separate shells, such as an upper shell 1003 and a lower shell 1004. In some embodiments, the upper shell 1003 and the lower shell 1004 may be locked by a screw or a structural design. The RF cable 1010 inside the cavity 1002 may be held tightly. In some embodiments of the present disclosure, the upper shell 103 and the lower shell 1004 of the shell 1001 may be an integral structure, or form a single piece. The cable 1010 may be introduced or from or pass through the cavity 1002.

The cavity 1002 may be limited spatially by the inner formation of the shell 1001. For example, the cavity 1002 may be segmented by one or more cross sections. In some embodiments, the cross section or the shape of the cross section may be circular or nearly circular to obtain a high quality of a sheath wave trap, since the magnetic loss may be relatively small in a magnetic circuit. In some embodiments, the cross section or the shape of the cross section may also be elliptic or another shape. In some embodiments, the cavity 1002 may accommodate only one cable. In some embodiments, the cavity 1002 may accommodate more than one cables. In some embodiments, the cable 1010 may be an assembled RF cable with a RF line for transmitting a magnetic resonance signal, an inner conductor including a DC cable, a wire shield for shielding the inner conductor, or the like, or a combination thereof. The shielding may be achieved by surrounding the inner conductor by a meshed metal wire. The inner conductor may be insulated relative to the outer conductor.

Figure 11:
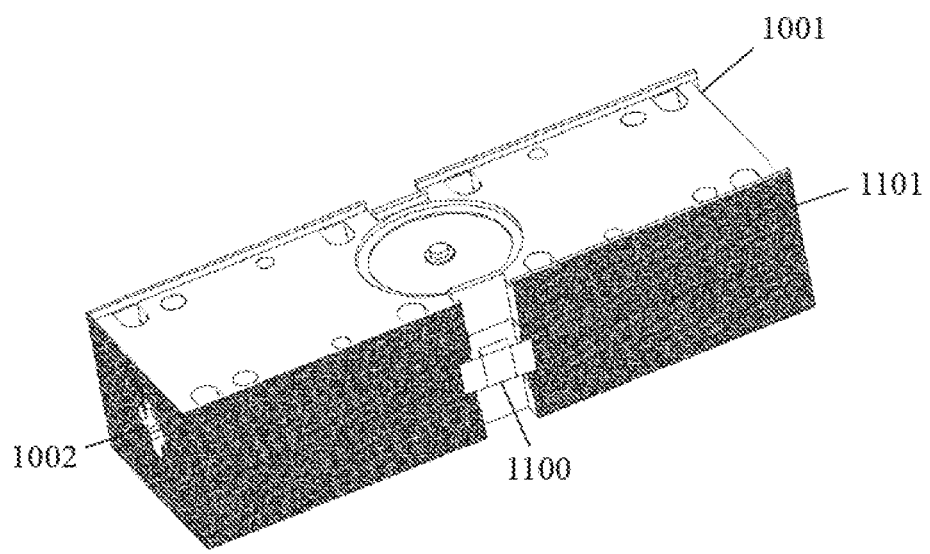
FIG. 11 is another schematic diagram of an exemplary line trapper in accordance with some embodiments of the present disclosure.

As shown in FIG. 11, the shell 1001 may include an electric conductor 1101. The electric conductor 1101 may be set on the surface outside the cavity 1002. In some embodiments, the electric conductor 1101 may be an electrically conductive layer including, for example, a metallization layer, a metal layer, or the like, or a combination thereof. The metallization layer is a layer coated or treated by a metal. The metal layer or the metallization layer may include copper, silver, zinc, or the like, or an alloy thereof, or any combination thereof. The electric conductor 1101 may include a break formed by, for example, at least one first gap. The gap may be bridged by at least a capacitive element 1100. The electric conductors 1101 adjacent to the first gap may contact the joints of the capacitive element 1100, respectively. A parallel resonant circuit may be formed by the electric conductor 1101 of the shell 1001 and the capacitive element 1100. The resonance frequency of the parallel resonant circuit may be tuned to an anticipated frequency. The tuning of the resonance frequency may include calculating the value of inductance and the value of capacitance. An inductor or a capacitor with a variable inductance value or a variable capacitance value may be used for the tuning of the resonance frequency.

Figure 12:
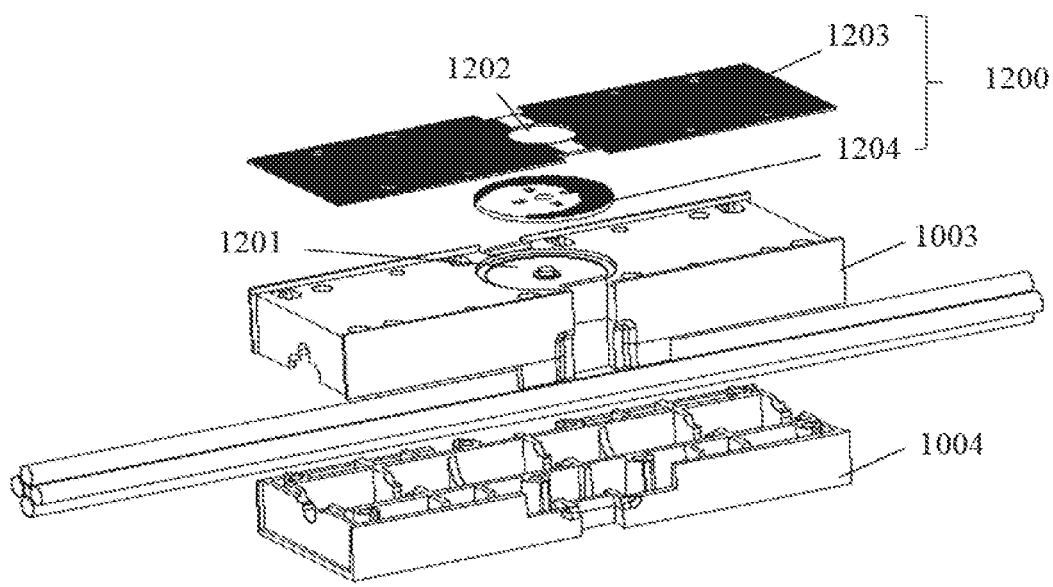
FIG. 12 is a detailed view of an exemplary line trapper as in FIG. 11 in accordance with some embodiments of the present disclosure.

As shown in FIG. 12, a capacitor element 1200 may be a plate capacitor in some embodiments of the present disclosure. The capacitor element may include a first electrode plate and a second electrode plate. The two electrode plates may be set against each other. In some embodiments, the first electrode plate may be a first circuit board 1203 with an electrically conductive layer including, for example, a metallization layer, a metal layer, or the like, or a combination thereof; the second electrode plate may be a second circuit board 1204 with an electrically conductive layer including, for example, a metallization layer, a metal layer, or the like, or a combination thereof. In some embodiments, the first electrode plate may be a first circuit board 1203 with a metal layer; the second electrode plate may be a second circuit board 1204 with a metallization layer. The metallization layer of the first circuit board 1203 may be separated by at least one second gap. The metal layer or the metallization layer may include copper, silver, zinc, or the like, or an alloy thereof, or any combination thereof. In some embodiments, the shape of the electrically conductive layer of the first circuit board 1203 and the second circuit board 1204 may be crescent, rectangular, trapezoidal, triangular, or the like, or any combination thereof. The overlapping area of the electrically conductive layers of the first circuit board 1203 and the second circuit board 1204 may form the electrode area of the capacitor element. In some embodiments of the present disclosure, the first circuit board 1203 and the second circuit board 1204 of the capacitor element may be a metal plate.

According to the capacitance formula $C=\varepsilon S/4\pi kd$, where C is a capacitance value, c is a dielectric constant, k is an electrostatic force constant, S is an electrode area, and d is a distance between two plates. The capacitance value may be varied by changing the overlapping area of the two electrode plates of the capacitor element in the case that, for example, other parameters are constant. According to the principle, the overlapping area of the two electrode plates may be varied by moving at least one of the first circuit board 1203 and the second circuit board 1204 of the tunable capacitor element. The capacitance value may be varied according to the change of the overlapping area.

The tunable capacitor element may be set on the side of the shell 1001. The first circuit board 1203 and the second circuit board 1204 of the tunable capacitor element may be connected with the shell 1001, respectively. For example, the first circuit board 1203 may be connected fixedly with the shell 1001, and the both ends of the second circuit board 1204 may be connected electrically with the electric conductor 1101 of the shell 1001. As another example, the second circuit board 1204 may be connected electrically with the shell 1001, and the second circuit board 1204 may be electrically insulating from the electric conductor 1101 of the shell 1001. The second circuit board 1204 may translate or rotate relative to the shell 1001 and the first circuit board 1203. The overlapping area of the electrically conductive layer of the first circuit board 1203 and the electrically conductive layer of the second circuit board 1204 may be varied when translating or rotating the second circuit board 1204 relative to the first circuit board 1203. Then the capacitance value of the tunable capacitor element may be varied.

In some embodiments of the present disclosure, the first circuit board 1203 may be connected electrically with the shell 1001, and the second circuit board 1204 may be fixed onto the shell 1001. The capacitance value of the tunable capacitor element 303 may be varied when translating or rotating the first circuit board 1203 relative to the second circuit board 1204.

In some embodiments, the shell 1001 may include a counter bore 1201. The counter bore 1201 may be configured to accommodate the second circuit board 1204. The second circuit board 1204 inside the counter bore 1201 may be connected movably with the shell 1001. A cross section or a shape of the cross section of the counter bore 1201 may be set according to a condition. For example, the cross section or the shape of the cross section may be set as the same as the shape of the second circuit board 1204, or may also be another shape. As another example, the depth of the counter bore 1201 may be set as about the same as the depth of the second circuit board 1204. When the second circuit board 1204 is inside the counter bore 1201, the shape and the inner diameter of the counter bore 1201 may satisfy the condition that the second circuit board 1204 may translate or rotate relative to the shell 1001.

In some embodiments, the first circuit board 1203 may include an opening 1202. The opening 1202 may be set against the second circuit board 1204. A cross section or a shape of the cross section of the opening 1202 may be set according to a condition. For example, the cross section or the shape of the cross section may be circular, nearly circular, rectangular, oval, or other shapes. The shape and the inner diameter of the opening 1202 may satisfy the condition that the overlapping area of the electrically conductive of the first circuit board 1203 and the second circuit board 1204 may be varied when translating or rotating the second circuit board 1204 relative to the first circuit board 1203.

As shown in FIG. 12, the tunable capacitor element may include a first circuit board 1203 and a second circuit board 1204, the two circuit boards may be set against each other. The shape of the first circuit board 1203 may be, for example, rectangular. The first circuit board 1203 may be fixed onto the shell 1001. A surface of the first circuit board 1203 against to the second circuit board 1204 may be covered with an electrically conductive layer. Both ends of the electrically conductive layer may be connected electrically with the electric conductor 1101 of the shell 1001. The electrically conductive layer may break by a second gap. The first circuit board 1203 may also include an opening 1202 thereon.

The second circuit board 1204 may be below the opening 1202 of the first circuit board 1203. The second circuit may be connected movably with the shell 1001. At least a portion of the second circuit board 1204 may be exposed or accessible through the opening 1202. The second circuit board 1204 may be translated or rotated through the opening 1202. The shape of the second circuit board 1204 may be circular, and the diameter of the second circuit board 1204 may be larger than the inner diameter of the opening 1202. The surface of the second circuit board 1204 against the first circuit board 1203 may be coated with an electrically conductive layer. The electrically conductive layer on the surface of the second circuit board 1204 may be of the shape of, for example, a crescent, an elliptic, or a rectangular, or the like, or the combination thereof. The overlapping area of the electrically conductive layer of the first circuit board 1203 and the electrically conductive layer of the second circuit board 1204 may be adjusted by rotating the second circuit board 1204. Then the capacitance value of the tunable capacitor element may be adjusted.

The shell 1001 may include a counter bore 1201 on the surface. The counter bore 1201 may be configured to accommodate the second circuit board 1204. The cross section of the counter bore 1201 may be circular. The inner diameter of the counter bore 1201 may be a little larger than the diameter of the second circuit board 1204. For instance, the inner diameter of the counter bore 1201 may be 2%, or 3%, or 5%, or 8%, or 10%, or more than 10% larger than the diameter of the second circuit board 1204. The depth of the counter bore 1201 may be about the same as the second circuit board 1204. For instance, the depth of the counter bore 1201 may be 99%, or 98%, or 96%, or 95%, or 92%, or 90%, or 88%, or 85%, or at least 80%, or at least 85% of the second circuit board 1204. The second circuit board 1204 may include an adjusting structure in order to adjust the second circuit board 1204. In some embodiments, the adjusting structure may be a hole, and also may be another structure that may allow adjusting of the second circuit board 1204.

In some embodiments of the present disclosure, the tunable capacitor element 303 may include a first circuit board 1203 and several second circuit boards 1204 set against the first circuit board 1203. The first circuit board 1203 may be break by several second gaps. The second circuit board 1204 may be set separately below a second gap. The several second circuit boards 1204 may be connected movably with the shell 1001. The capacitance value of the tunable capacitor element may be adjusted by translating or rotating at least one second circuit board 1204.

Figure 13:
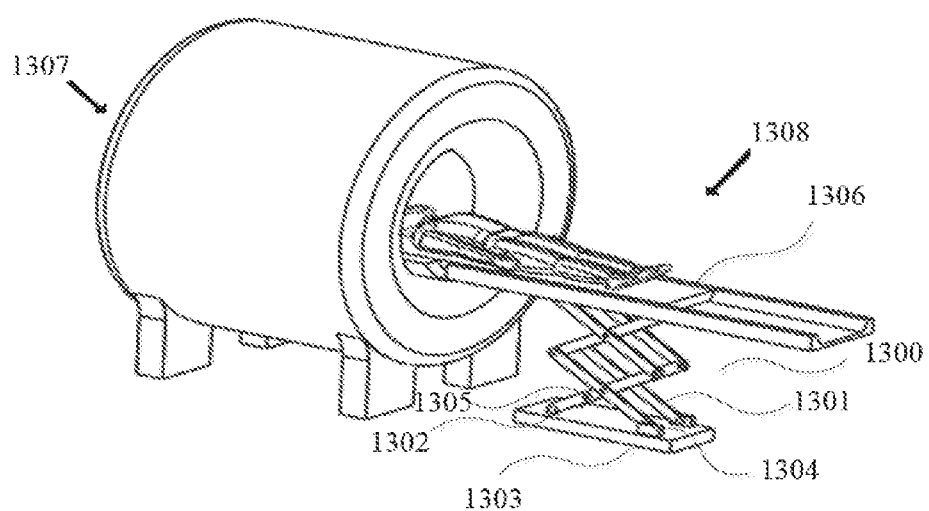
FIG. 13 is a schematic diagram of an exemplary elevating module in accordance with some embodiments of the present disclosure.

FIG. 13 is a schematic view of the structure of an elevating module according to some embodiments of the present disclosure.

The elevating module used in the displacement amplification mechanism and the embodiment of the elevating module used in medical system are described in detail, in which an MRI device that may need accurate control of a transport apparatus is described as an example.

As shown in FIG. 13, an MRI device may include an imaging section 1307 and a bed section, wherein the bed section may include a patient bed unit 1306, a transferring unit 1300, and an expansion bracket 1301

Figure 14:
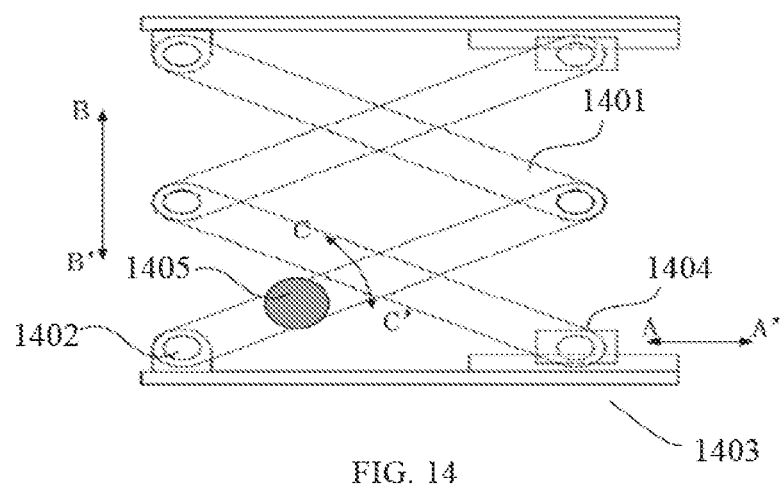
FIG. 14 is another view of an exemplary elevating module in accordance with some embodiments of the present disclosure.

The elevating module 1300 may be used to drive the patient bed unit 1306 to move upwards and/or downwards vertically along the B-B' direction as shown in FIG. 13. The elevating mechanism 1300 may include an expansion bracket 1301 and a foundation 1303. In the embodiment as illustrated in FIG. 13, the expansion bracket 1301 may be in a double shear structure. In some embodiments, the expansion bracket may be in a single shear structure or another suitable structures. The end 1302 in the bottom part of the expansion bracket 1301 may rotate (as indicated by C-C' in FIG. 14). The end 1302 may be fixed onto the foundation 1303. A slider 1304 may be installed on the other end to coordinate with the rotation of the fixed end 1302. The slider 1304 may slide (as indicated by A-A' in FIG. 14) within the foundation 1303 to implement the upward and downward movement of the patient bed 1306.

The elevating module may include a controller, a switching circuit, a trigger 1305, and a displacement amplification mechanism. The trigger 1305 may be installed on the expansion bracket 1301, when the expansion bracket 1301 drives the vertical movement of the patient bed 1306. The trigger 1305 may rotate (as indicated by C-C' illustrated in FIG. 14) together with the expansion bracket 1301 and trigger the switch on one side of the expansion bracket 1301. The controller may receive a signal transmitted from the switching circuit and control the movement of the elevating mechanism 1300.

Figure 15:
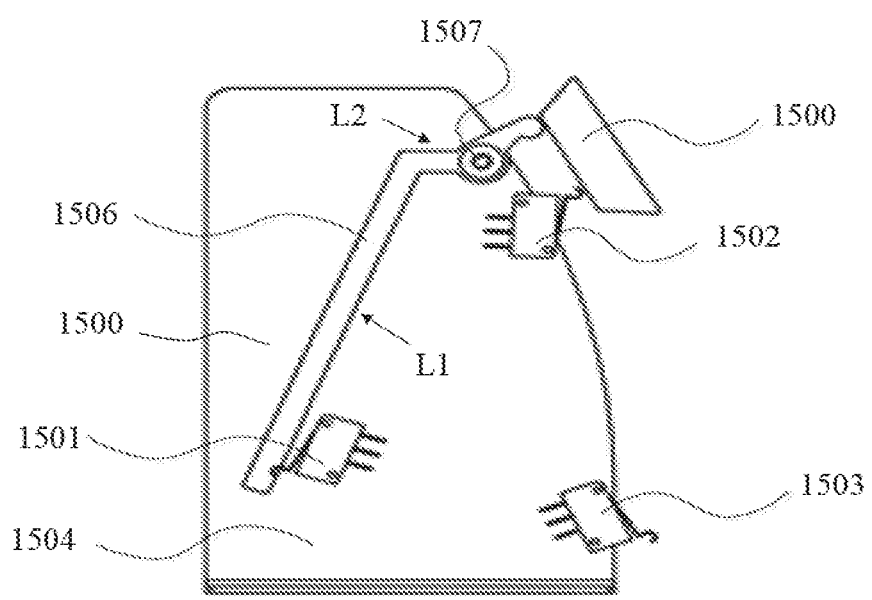
FIG. 15 is a schematic diagram of an exemplary leverage structure together with switches in accordance with some embodiments of the present disclosure.

As shown in FIG. 15, there may be three switches in the switching circuit: the $1^{st}$ switch 1501; the $2^{nd}$ switch 1502; and the $3^{rd}$ switch 1503. One or more of all three switches may be installed on a bracket 1504 on one side of the expansion bracket 1301.

The $1^{st}$ switch 1501 may be an upward movement stop switch used to generate an upward movement stop signal. When the patient bed 1306 moves upwards, it may first be slowed down and then stopped, the trigger 1305 may trigger the 1st switch by using the lever 1506. The second end of the lever 1506 may be higher than the $2^{nd}$ switch. A pin roll 1507 may be placed at a position in bracket 1504; the $1^{st}$ switch 1501, away from the pin roll 1507, may be placed at a position in bracket 1504 lower than the position of the pin roll 1507, in order to implement the function of amplification of the lever 1506 and increase the sensitivity of the $1^{st}$ switch. However, a person with ordinary skill in the art may figure out that the sensitivity may be increased if L1 is greater than L2, therefore all the positions that satisfy the condition described above are acceptable.

The $2^{nd}$ switch 1502 may be a speed-reducing switch used to generate a speed-reducing signal. The $2^{nd}$ switch may be placed in a relatively high position in the bracket 1504. When the patient bed 1306 is moving upwards, the trigger 1305 and the expansion bracket 1301 may move upwards together and trigger the $2^{nd}$ switch. The $2^{nd}$ switch may generate a speed-reducing signal, and the controller may control the expansion bracket 1301 to reduce the speed of the upward movement by driving, for example, an electric motor. Because the need for high accuracy in terms of the position of the patient bed toward the highest position in an MM device, in order to reduce the effect of the inertia, the speed may be reduced before approaching the highest point. However, in other medical systems that do not need high accuracy in terms of the position of the patient bed, the $2^{nd}$ switch may be optional.

The $3^{rd}$ switch 1503 may be a downward movement stop switch used to generate a downward movement stop signal. The $3^{rd}$ switch 1503 may be placed in a relative lower position in the bracket 1504. When the patient bed 1306 moves downwards, the trigger 1305 and the expansion bracket 1301 may move downwards together and trigger the $3^{rd}$ switch 1503. The $3^{rd}$ switch may generate a stop signal, and the controller may control the expansion bracket 1301 to stop the downward movement by driving, for example, an electric motor.

In some embodiments of the present disclosure, the $1^{st}$ switch 1501, the $2^{nd}$ switch 1502, and the $3^{rd}$ switch 1503 may be mechanical limit switches. When the patient bed 1306 is at the highest position, both the $1^{st}$ switch 1501 and the $2^{nd}$ switch may be suppressed. At this time, if the trigger 1305 moves downwards with a small displacement in the vertical direction, the small displacement may be amplified and transferred to the first end of the lever 1506 to generate a larger displacement in the first end of the lever 1506, and the 1$^{st}$ switch 1501 may be released, thereby determining that the patient bed 1306 isn't at the highest position. Therefore, wrong determination (whether the patient bed 1306 is at its highest position) may be solved using the displacement amplification mechanism and the need for high positional accuracy in the MM device at the highest position may be satisfied.

A person having ordinary skill in the art may easily be aware that the bracket 1504 for fixing a switch may be a bracket for matching the moving path of the trigger block 1500, or a shell structure for surrounding the expansion bracket 1301 or any other component of fixation. A person having ordinary skill in the art may also know the structure when the said switch and the lever 1506 may be mounted on the expansion bracket 1301, and the trigger block 1500 may be mounted on the bracket 1504.

In some embodiments, the three switches may be locked under normal conditions. For instance, when the switch is pressed down, signals received by the controller is 0 or 1. The controller may receive different messages (exemplified in Table 1) by sensing the different position of the trigger block 1500. According to Table 1, different signals showing different conditions of a patient bed may be presented according to specific states of the switches among which the "error" condition may indicate that the controller received an error massage.

TABLE 1

| Condition | First Switch | Second Switch | Third Switch |
| --- | --- | --- | --- |
| Switch not connected | 0 | 0 | 0 |
| Highest position | 0 | 0 | 1 |
| Error | 0 | 1 | 0 |
| Speed-reducing position | 1 | 0 | 1 |
| Error | 0 | 1 | 1 |
| Error | 1 | 0 | 0 |
| Lowest position | 1 | 1 | 0 |
| Middle position | 1 | 1 | 1 |

As shown in Table 1, when the wires of the three switches are not connected, the three switches are all in off condition, and the controller may receive the signal of "000" through circuit design. When the patient bed 1306 is in the middle position, and three switches are all connected and not pressed, the three switches may all be locked, and the controller receive a message of "111." Therefore, the signals received by the controller may represent the condition of the wires not connected and the condition of patient bed 1306 being in the middle position, respectively. This may avoid the wrong operation to the patient bed 1306 while the wires of the switches are not connected, and improve the reliability and safety of the elevating module The process of elevating module is shown below: the controller may control the movement of the elevating mechanism 1300. The patient bed 1306 arise and then trigger block 1500 do rotary motion with the extendable stick 1301 and raise along the arc. When the trigger block 1500 press the second switch, the controller receive a signal of "101" sent by the switch circuit and slow down the elevating mechanism 1300. When the patient bed 1306 continues arise, the trigger block 1500 may push the lever 1506 rotating around the pin roll 1507 while pressing the second switch 1502, and then press the first switch 1501. At this time, the switch circuit may generate and/or forward the signal of "001" representing that the patient bed 1306 is in the highest position. The controller may receive the signal and stop the elevating mechanism 1300. When the patient bed 1306 is in the lowest position, the switch circuit may generate and/or forward the signal of "110" representing that the patient bed 1306 is in the lowest position. The controller may receive the signal and stop the elevating mechanism 1300.

During the process, if the controller receives an error signal shown in Table 1, the patient bed 1306 may stop moving. An alert may be provided to notify the situation.

During the process, the switch circuit may generate and/or forward to the controller different signals representing different conditions of the patient bed 1306. For instance, according to Table 1, when the switch wires are not connected and the patient bed 1306 is at the middle position, the switch circuit may generate and/or forward different signals to the controller, respectively. Thus, the controller may distinguish the difference between the state that the switch wires are not connected from that the patient bed 1306 is at the middle position, thereby avoiding a wrong operation to the patient bed 1306 while the switch wires are not connected, and improve the reliability and safety of the MRI device.

Because of the low accuracy requirement when the patient bed 1306 is located toward the lowest position in an MRI device, a speed-reducing switch may be absent in some embodiments. However, it will not be a limitation in the scope of this disclosure. A speed-reducing switch at the lowest position may be included to provide a highly accurate control when the patient bed 1306 is in the lowest position.

Figure 16A:
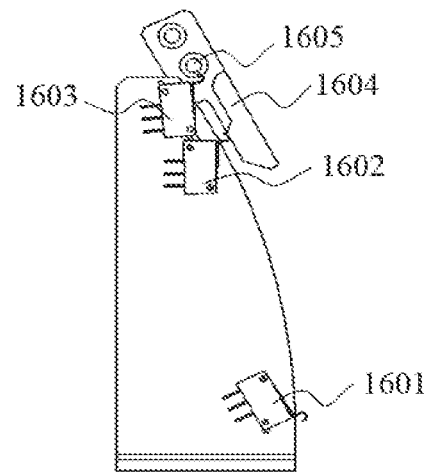
FIGS. 16A and 16B are schematic diagrams of an exemplary leverage structure together with switches in accordance with some embodiments of the present disclosure.
Figure 16B:
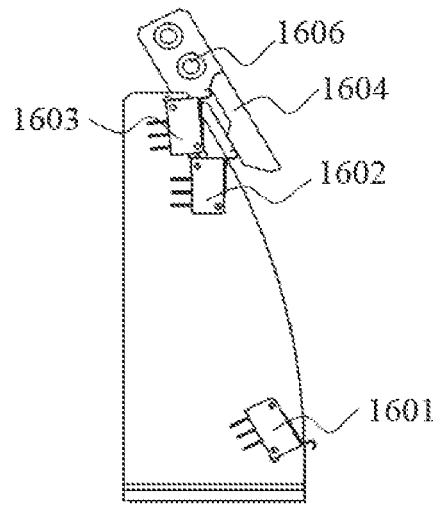

As shown in FIGS. 16A and 16B, the positioning of the three switches 1601, 1602, and 1603 may be altered in such a way that the activating surfaces of the switch 1602 and the switch 1603 do not lie on the same plane. It may then be such that the switch 1602 and the switch 1603 may be activated separately. As illustrated in FIG. 16A and FIG. 16B, when the speed reducing switch 1602 has been activated, the distance between the touching surface to activate the switch 1603 and the switch 1603 itself may be close, and thus the time to activate the switch 1603 may be reduced. It may then be applicable to adapt a reduced speed of the elevating module to reach the switch 1603.

The elevating module including a displacement amplification mechanism on the bracket as disclosed herein may have an improved sensibility and accuracy. The normally locked switch may improve reliability and safety of the elevating module.

It also should be noted that the above embodiments are for illustration purposes and not intended to limit the scope of the present disclosure. For persons having ordinary skill in the art, the image processing method may be variable, changeable, or adjustable based on the spirits of the present disclosure. In some embodiments, the steps may be added, deleted, exchanged, replaced, modified, etc. For example, the pre-processing and/or post-processing may be deleted. For another example, the order of the steps in the image processing method may be changed. For still another example, some steps may be executed repeatedly. However, those variations, changes and modifications do not depart from the scope of the present disclosure.

The invention claimed is:
1. A patient bed comprising:
 a bed board for accommodating a patient;
 a bedstead for supporting the bed board;
 at least two sliding wheel sets for allowing the bed board to move horizontally relative to the bedstead along a longitudinal direction of the bed board, wherein each of the at least two sliding wheel sets includes a plurality of sliding rollers along the longitudinal direction of the bed board; and at least one buffer roller on a side of a sliding wheel set of the at least two sliding wheel sets, the at least one buffer roller and the sliding wheel set being along the longitudinal direction of the bed board, wherein a radius of a buffer roller of the at least one buffer roller is less than a sliding roller of the sliding wheel set, wherein the sliding wheel set and the at least one buffer roller are restricted by a same flat surface of a guide rail.

2. The patient bed of claim 1, wherein a first distance between a buffer roller of the at least one buffer roller and an adjacent sliding roller of the plurality of sliding rollers is less than a second distance between a sliding roller of the plurality of sliding rollers and an adjacent sliding roller of the plurality of sliding rollers.

3. The patient bed of claim 2, wherein the first distance is within the range from 1 millimeter to 10 millimeters.

4. The patient bed of claim 1, wherein the at least one buffer roller includes two buffer rollers on both sides of the sliding wheel, respectively.

5. The patient bed of claim 4, wherein the two buffer rollers are symmetrical on the both sides of the sliding roller set.

6. The patient bed of claim 1, further comprising at least one first guide rail facilitating movements of the at least two sliding roller sets and the at least one buffer roller.

7. The patient bed of claim 1, further comprising a drag chain structure between the bed board and the bedstead.

8. The patient bed of claim 7, wherein the drag chain structure comprises a bent feature that moves along in a direction which is opposite to that of the bed board.

9. The patient bed of claim 8, wherein a first end of the drag chain is fixed upon the bed board, and a second end of the drag chain is fixed upon the bedstead.

10. The patient bed of claim 9, wherein the first end of the drag chain is fixed upon the bed board via a fastener.

11. The patient bed of claim 10, wherein the fastener includes at least one of a screw, a catch, or a buckle.

12. The patient bed of claim 9, wherein the second end of the drag chain is fixed upon a groove of the bedstead.

13. A transport apparatus for moving a patient in an imaging system, the apparatus comprising:
a patient bed including:
a bed board for accommodating a patient;
a bedstead for supporting the bed board;
at least two sliding wheel sets for allowing the bed board to move horizontally relative to the bedstead along a longitudinal direction of the bed board, wherein each of the at least two sliding wheel sets includes a plurality of sliding rollers along the longitudinal direction of the bed board; and
at least one buffer roller on a side of a sliding wheel set of the at least two siliding wheel sets, the at least one buffer roller and the sliding wheel set being along the longitudinal direction of the bed board, wherein a radius of a buffer roller of the at least one buffer roller is less than a sliding roller of the sliding wheel set, wherein the sliding wheel set and the at least one buffer roller are restricted by a same flat surface of a guide rail.

14. The transport apparatus of claim 13, further comprising:
an elevating module for vertically lifting the patient bed to a desired position along a first direction of the imaging system.

15. The transport apparatus of claim 14, wherein the elevating module comprises a movement amplifier, a sensor, and a controller.

16. The transport apparatus of claim 15, wherein the elevating module further comprises a downward movement stop switch or a rising movement switch.

17. The transport apparatus of claim 15, wherein the elevating module further comprises a speed reducing switch.

18. The transport apparatus of claim 14, further comprising:
a line trapper.

19. The transport apparatus of claim 18, wherein the line trapper is of an elliptical shape.

20. The transport apparatus of claim 13, wherein the imaging system includes at least one of a magnetic resonance imaging (MRI) system, a treatment system, or an examination system.

* * * * *